(12) United States Patent
Zerick et al.

(10) Patent No.: US 11,126,917 B2
(45) Date of Patent: Sep. 21, 2021

(54) SYSTEM AND METHOD FOR ESTIMATING POTENTIAL INJURIES FROM A VEHICULAR INCIDENT

(71) Applicant: AT&T Intellectual Property I, L.P., Atlanta, GA (US)

(72) Inventors: Juliette Zerick, Alpharetta, GA (US); William Cottrill, Canton, GA (US); Sheldon Meredith, Roswell, GA (US); Ravishankar Doejode, Johns Creek, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 260 days.

(21) Appl. No.: 15/852,656

(22) Filed: Dec. 22, 2017

(65) Prior Publication Data

US 2019/0197414 A1    Jun. 27, 2019

(51) Int. Cl.
  *G06N 5/04* (2006.01)
  *G07C 5/08* (2006.01)
  *G06N 20/00* (2019.01)

(52) U.S. Cl.
  CPC .............. *G06N 5/04* (2013.01); *G06N 20/00* (2019.01); *G07C 5/085* (2013.01)

(58) Field of Classification Search
  CPC .......... G06N 5/04; G06N 20/00; G06N 7/005; G06N 99/00; G06N 5/046; G06N 3/0445; B60R 21/013; B60R 21/0132; B60R 21/0136; B60R 21/01558; G07C 5/085; G07C 5/0808; G07C 5/08; G07C 5/0816; A61B 5/01; A61B 5/02; A61B 2505/00; A61B 5/162; A61B 3/113
  See application file for complete search history.

(56) References Cited

U.S. PATENT DOCUMENTS

| | | | |
|---|---|---|---|
| 6,690,302 B1 | 2/2004 | Inomata | |
| 6,732,020 B2 * | 5/2004 | Yamagishi | ............. G08G 1/205 340/436 |
| 6,758,812 B2 | 7/2004 | Lang | |

(Continued)

FOREIGN PATENT DOCUMENTS

CN      103942454 A    7/2014

OTHER PUBLICATIONS

Xu et al.; "Ubiquitous Data Accessing Method in IoT-Based Information System for Emergency Medical Services"; IEEE Transactions on Industrial Informatics; vol. 10 No. 2; May 2014; p. 1578-1586.

(Continued)

*Primary Examiner* — Luis A Martinez Borrero
(74) *Attorney, Agent, or Firm* — BakerHostetler (57) ABSTRACT

A system for predicting injuries includes a plurality of sensors configured to generate sensor data and an apparatus having an input-output interface and a processor coupled to the input-output interface and wherein the processor is coupled to a memory, the memory having stored thereon executable instructions that when executed by the processor cause the processor to effectuate operations including receiving the sensor data, applying analytics to the sensor data, based on the applying step, predicting a likely injury, and transmitting a report based on the predicting step.

16 Claims, 5 Drawing Sheets

(56) References Cited

U.S. PATENT DOCUMENTS

| | | | | |
|---|---|---|---|---|
| 6,954,135 B1* | 10/2005 | Yoshioka | | B60R 25/04 340/426.2 |
| 7,158,016 B2* | 1/2007 | Cuddihy | | G08B 25/016 340/436 |
| 7,466,235 B1 | 12/2008 | Kolb et al. | | |
| 7,832,762 B2* | 11/2010 | Breed | | B60R 21/013 280/735 |
| 8,346,703 B2* | 1/2013 | Gee | | A61B 5/0015 706/46 |
| 8,680,989 B2 | 3/2014 | George | | |
| 8,825,277 B2* | 9/2014 | McClellan | | G06Q 10/06 701/32.2 |
| 9,020,690 B2* | 4/2015 | McKown | | G08B 25/10 701/33.7 |
| 9,235,687 B2* | 1/2016 | Wanami | | G01P 15/00 |
| 9,254,804 B2* | 2/2016 | Wanami | | G06K 9/00362 |
| 9,290,145 B2 | 3/2016 | Mader et al. | | |
| 9,317,983 B2* | 4/2016 | Ricci | | B60R 25/1004 |
| 9,539,969 B2* | 1/2017 | Crandall | | B60R 21/01526 |
| 9,650,007 B1* | 5/2017 | Snyder | | B60R 21/0132 |
| 9,852,599 B1* | 12/2017 | Slavin | | G08B 21/043 |
| 9,969,344 B1* | 5/2018 | Kolasi ski | | G08B 25/016 |
| 10,241,511 B2* | 3/2019 | Regmi | | A61B 5/01 |
| 10,417,713 B1* | 9/2019 | Brandmaier | | B60R 21/0136 |
| 10,636,516 B2* | 4/2020 | Cohen | | G16H 15/00 |
| 2001/0040504 A1* | 11/2001 | Gehlot | | B60R 25/33 340/426.1 |
| 2002/0103622 A1* | 8/2002 | Burge | | G06F 19/00 702/183 |
| 2003/0212475 A1* | 11/2003 | Yamagishi | | G08G 1/205 701/1 |
| 2005/0040937 A1* | 2/2005 | Cuddihy | | G08B 25/016 340/436 |
| 2008/0306996 A1* | 12/2008 | McClellan | | G06Q 10/06 |
| 2009/0000377 A1* | 1/2009 | Shipps | | A61B 5/4064 73/514.16 |
| 2010/0210237 A1* | 8/2010 | Tomer | | H04M 11/04 455/404.2 |
| 2011/0055133 A1* | 3/2011 | Gee | | A61B 5/0015 706/46 |
| 2011/0130111 A1* | 6/2011 | Crandall | | B60R 21/015 455/404.1 |
| 2011/0181419 A1* | 7/2011 | Mack | | G01L 1/26 340/573.1 |
| 2011/0184663 A1* | 7/2011 | Mack | | G01L 1/26 702/41 |
| 2012/0094628 A1* | 4/2012 | Mader | | H04W 4/90 455/404.1 |
| 2013/0332026 A1* | 12/2013 | McKown | | B60R 21/013 701/33.7 |
| 2014/0135598 A1* | 5/2014 | Weidl | | G16H 50/20 600/301 |
| 2014/0195169 A1* | 7/2014 | Wanami | | G16H 50/20 702/19 |
| 2014/0207341 A1* | 7/2014 | Wanami | | B60R 21/0136 701/46 |
| 2014/0221781 A1* | 8/2014 | Schrauf | | A61B 5/02055 600/301 |
| 2014/0300739 A1* | 10/2014 | Mimar | | G08B 21/06 348/148 |
| 2014/0306826 A1* | 10/2014 | Ricci | | B60R 25/20 340/573.1 |
| 2015/0196252 A1* | 7/2015 | Iuliano | | A61B 5/6803 600/301 |
| 2015/0246673 A1* | 9/2015 | Tseng | | B60W 30/16 701/23 |
| 2015/0365810 A1* | 12/2015 | Yamaguchi | | G06K 9/00845 701/32.2 |
| 2016/0019352 A1* | 1/2016 | Cohen | | G16H 15/00 705/3 |
| 2016/0086491 A1* | 3/2016 | Choi | | H04M 11/04 340/425.5 |
| 2016/0125155 A1 | 5/2016 | Shelter | | |
| 2016/0142894 A1 | 5/2016 | Papakonstantinou et al. | | |
| 2017/0017766 A1 | 1/2017 | Giraud | | |
| 2017/0174163 A1* | 6/2017 | Korthauer | | B60R 21/01552 |
| 2018/0043901 A1* | 2/2018 | Kim | | A61B 5/021 |
| 2018/0126983 A1* | 5/2018 | Beauvais | | B60W 10/04 |
| 2018/0365772 A1* | 12/2018 | Thompson | | G06Q 50/30 |
| 2019/0066225 A1* | 2/2019 | Thompson | | G06Q 10/10 |
| 2020/0380404 A1* | 12/2020 | Rakshit | | A62B 99/00 |

OTHER PUBLICATIONS

Fernandes et al.; "Mobile Application for Automatic Accident Detection and Multimodal Alert"; IEEE Vehicular Technology Conf.; 2015; 5 pages.

* cited by examiner

SYSTEM AND METHOD FOR ESTIMATING POTENTIAL INJURIES FROM A VEHICULAR INCIDENT

TECHNICAL FIELD

This disclosure relates generally to using an array of sensors to generate data relating to an accident, and more specifically, to a system and method for using the sensor data to estimate injuries which may have resulted from an accident.

BACKGROUND

In an emergency situation such as a motor vehicle accident, it is helpful to be able to automatically notify public safety personnel, first responders and care centers about the accident and that injuries may have occurred. There are service such as OnStar® which are able to detect collisions and alert emergency responders automatically.

However, none of the existing systems provide any estimates of potential injuries that may have been suffered in a traffic accident. Such injuries may include, for example, internal damage to organs, the potential for fracture or shattering of bone, the strength and severity of whiplash.

There is also a relatively new theory relating to trauma kinematics which includes the study a vehicular accident may have with respect to potential injuries. For example, a rear impact collision may force the torso of an occupant forward. If a head restraint is not properly positions, the head may be hyperextended over the top of the seat prior to being forced forward, causing a whiplash effect. Similarly, a lateral impact from, for example, an accident in which a vehicle is T-boned at an intersection may result in lateral motion injuries to an occupant of the vehicle which may, for example, include a compression or fracturing of a clavicle, ribs or pelvic bones or an injury to the organs that are situated within the torso. Other types of accidents, i.e., rollover, rotational impact, or other types of accidents, may result in injuries to the occupants consistent with the type of accident.

The time required to diagnose a patients injuries is critical. What is needed is a system and method by which injuries may be estimated and transmitted to a PSAP, an ambulatory vehicle or an urgent care center as soon as possible after an accident so as to decrease any life-threatening delay.

SUMMARY

The present disclosure is directed to a system for predicting injuries including a plurality of sensors configured to generate sensor data, an input-output interface, and a processor coupled to the input-output interface and wherein the processor is coupled to a memory, the memory having stored thereon executable instructions that when executed by the processor cause the processor to effectuate operations including receiving the sensor data, applying analytics to the sensor data, based on the applying step, predicting a likely injury, and transmitting a report comprising the likely injury based on the predicting step. The applying step may include applying trauma kinematics analysis to the sensor data. The plurality of sensors may include a first set of sensors configured to monitor motions of a vehicle and a second set of sensors configured to monitor motions of a person and wherein the applying step may include applying trauma kinematics analysis to the first sensor data and the second sensor data. The operations may further include receiving additional data inputs and the applying step comprises applying analytics to a combination of the sensor data and the additional data inputs. In an aspect, the additional data inputs may include historical patient data. In an aspect, the additional data inputs may include one of text inputs, voice inputs and screen inputs. The analytics may include comparing the sensor data with historical sensor data and comparing the predicted injury with other historical predicted injuries. The operations may further include recording the likely injury in the memory. The transmitting step may include transmitting the report to one of a care facility and a first responder.

The disclosure may also be directed to a method including receiving sensor data from a plurality of sensors, analyzing sensor data, applying trauma kinematics to the analyzed sensor data, and predicting an injury based on the applying step and in an aspect, may include transmitting a report comprising the predicted injury wherein the transmitting step may include transmitting the report to one of a care facility and a first responder. In an aspect, the sensor data is received wirelessly by an application operating in a controller and wherein the controller is a user device or alternatively the controller is located within a connected vehicle. The sensor data may include first sensor data in which the sensors are connected to a vehicle and second sensor data wherein the sensors are connected to a person. The method may include wherein the first sensor data and the second sensor data are correlated and the applying step applies trauma kinematics to the correlated first sensor data and the second sensor data. The correlated first sensor data and the second sensor data may be compared to historical sensor data and in an aspect, the predicted injury may be compared to an historical record of injuries.

BRIEF DESCRIPTION OF THE DRAWINGS

In the following description, for purposes of explanation, numerous specific details are set forth in order to provide an understanding of the variations in implementing the disclosed technology. However, the instant disclosure may take many different forms and should not be construed as limited to the examples set forth herein. Where practical, like numbers refer to like elements throughout.

DETAILED DESCRIPTION

Overview. As detailed herein, the present disclosure is directed to a system and method for predicting injuries from an automobile accident and providing those predictions to first responders and care centers. While the example of an automobile accident is used, that is exemplary only and the system and method of the present disclosure is useful for a variety of other applications in which sensors may measure the kinematic impact of trauma inducing events, process those sensor data in real time or near real time, and convey preliminary analysis to first responders or urgent care facilities. By knowing just what types of injuries to expect, emergency responders can better prepare and begin lifesaving treatment immediately, rather than waiting for an MRI or other diagnosis at a care center. For example, a broken bone may puncture arteries (causing massive subdermal hemorrhaging and the formation of deadly blood clots) and strong whiplash can cause injuries to the spine and brain (probable concussion and paralysis)—all injuries that would not be readily apparent at the scene of an accident, and definitely not predictable from only knowing the point of impact.

As such, the present disclosure may include a system having multiple sensors positioned strategically in a vehicle. Such sensors may, for example, include sensors on the bumpers, hood, tires, roof, and doors on the exterior of a vehicle and steering wheels, headliners, dashboards, interior door panels and the like on the interior of a vehicle. Cooperating with those sensors may be sensors embodied within articles of clothing to be worn by a person, including for example, sensors included in coats, jackets, sweaters, pants, belts, shirts, dresses, shoes, caps, hats, and undergarments. Sensors may also be included in other articles such as, for example, athletic equipment, uniforms, and emergency gear. Finally, sensors may also be positioned attached to or within a person's body. All such sensors may be in wireless communication with a controller, the controller being part of a connected car, a smart phone, a tablet, or any other type of controller. Upon impact, the sensors may wirelessly transmit data to the controller or controllers, conveying information such as force, velocity, direction, and other relevant data. The controller may then process the sensor data locally or communicate the sensor data to a server, perhaps a server at a public safety access point (PSAP) or other server for further processing to determine the likely types and severity of any potential injuries. The server, or in the case of the controller processing the sensor data locally, would then transmit the analysis results to a first responder, urgent care facility, PSAP or other relevant destination whereby patients may be treated in a more expeditious manner.

A mobile emergency application operating on a mobile device or hosted in a connected vehicle may be used. For the purposes of this disclosure, the term "mobile emergency application" is used interchangeably with "client application" unless otherwise specified. In addition to receiving sensor data, the emergency mobile application may receive other inputs, including voice inputs or other data inputs from a keyboard or interactive screen, for example, that may detect critical keywords or phrases like dying, bleeding, concussion, or the like to assist in the determination of the potential injures. In an embodiment, the patient, witness or companion may manually interact with the mobile emergency application, either by answering questions or entering information free form or from a predetermined menu.

In an aspect, the mobile device and/or connected-car may provide a remote server or ambulatory vehicles additional data including GPS-quality location information. A software application running on server may interpret the characteristics of the accident using the sensor data, which may, for example, include codes for a heart attack, severe cut, eye injury, burns, etc. and perhaps a severity index. This permits a handoff of the injured patient to the ambulance personnel prior to arrival at a hospital or urgent care center such that paramedics experts may render life-saving skills using emergency equipment to stabilize and treat the patient and begin the coordination with the hospital or urgent care center using the advanced diagnostics. Hospitals or urgent care centers will be referred to broadly herein as care centers.

Figure 1:
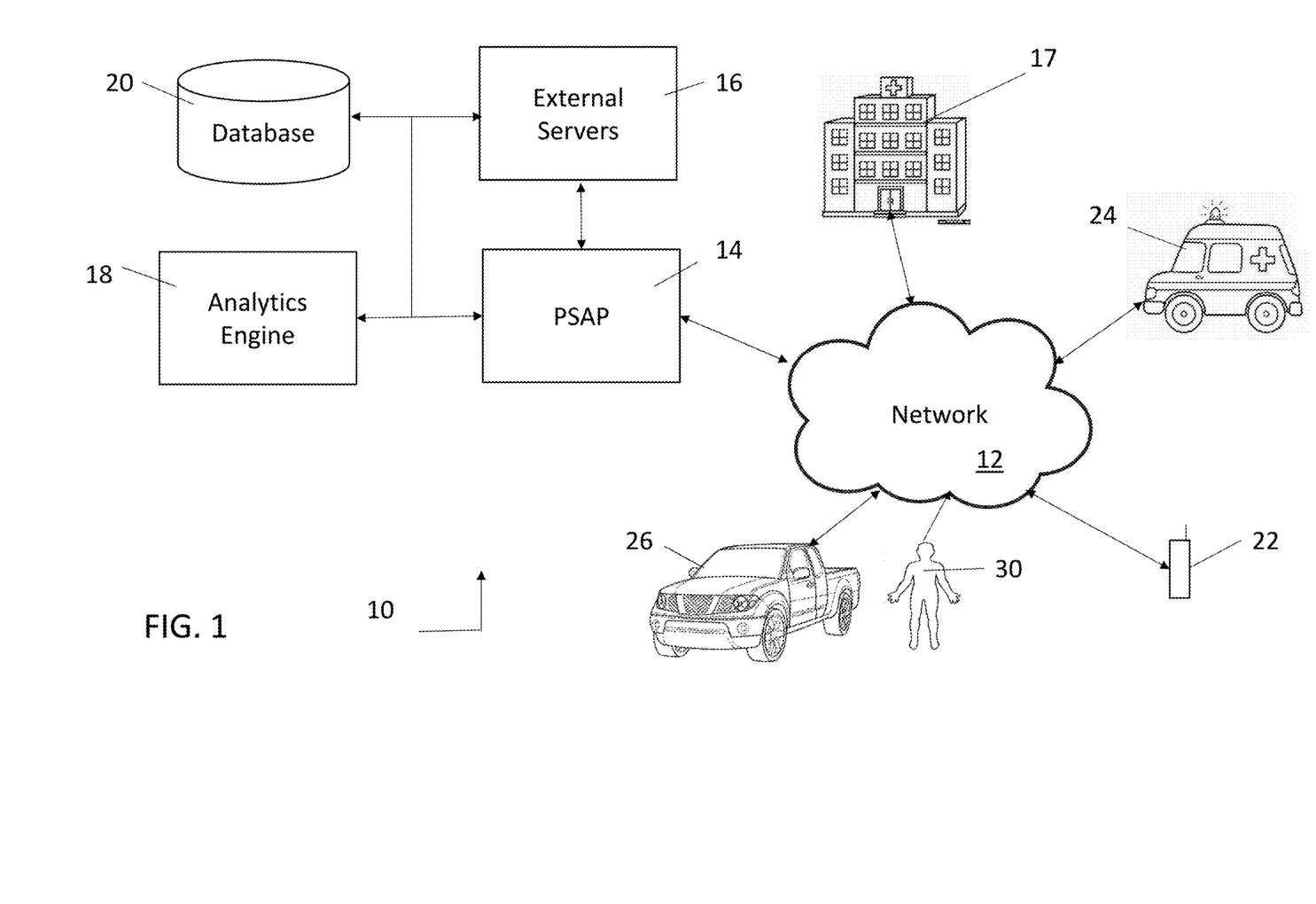
FIG. 1 is a representation of an exemplary operating environment for a Public Safety Access Point (PSAP) in communication with first responder vehicles and an emergency application in a connected vehicle, an individual accident victim, and/or smartphone.

System Environment. With reference to FIG. 1, there is shown a system 10 in which the present disclosure may operate. Central to the system is network 12, which may be a combination of wireless and/or wired network communication systems. The network 12 may include components of the Public Switched Telephone Network (PSTN) as well as wireless network systems including 3G, 4G/LTE, 5G, WiFi, WiMAX, and any other wireless network communications system now known or to be developed in the future. The network 12 and voice and data communications across the network 12 is generally known by those skilled in the art.

In communication with the network 12 may be a PSAP gateway 14. A PSAP gateway 14 is not required for the present disclosure and is used as an example only for the purposes of this written description. Functionally, the PSAP gateway 14 can be any type of server located at a hospital or urgent care center, a PSAP, a third party service provider, a wireless service provider, or any other remote entity that provides a server. The server may be discrete or reside in a cloud-based operational environment. The PSAP gateway 14 may be in communication with database 20. The database 20 may be local or reside in a cloud-based environment. The database 20 may include maps of roads and other transportation infrastructure, an identification of first responder ambulatory vehicles and their capabilities and locations, any other data which may be relevant to the systems and methods of the present disclosure.

Database 20 may also include location information, capacities and capabilities of care centers including hospitals, emergency rooms, doctors, heliports, nursing homes, temporary or permanent shelters, trauma units or any other location wherein a patient may obtain medical care. For each such care location, there may be stored in database 20 the capabilities or specialties available at each care location, including for example, trauma centers, surgical capabilities, first aid, orthopedics, x-rays, burn specialists or any other type of medical specialty or capability.

While client application 42 may be used to provide the analytics, in an aspect such analytics may be provided by analytics 18 or a combination of the two. As such, database 20 may also contain information relating to individuals' medical history. Database 20 may also contain historical data on vehicular accidents and injuries associated therewith. For example, database 20 may include sensor data compiled from a vehicle 26 involved in an accident, sensor data compiled from a person 30 having sensors attached to clothing or the body that was involved in the accident, and a diagnosis of actual injuries suffered by the person 30. Database 20 may include diagnostic codes for reporting potential injuries and to insurance companies. This may be useful in obtaining pre-authorization when required for certain procedures or hospital admissions. As such, the database 20 may include information for an analytics engine 18 to apply machine learning techniques to diagnose future injuries as described in more detail below with respect to analytics engine 50.

Continuing with the description of the operating environment in FIG. 1, the PSAP server 14 may be in communication with external servers 16 to obtain additional information. External servers may, for example, provide access to other data and programs not contained within the PSAP server 14 or other servers or database 20. For example, such additional information may include, but is not limited to, real time traffic reports and conditions, weather conditions, patient health records, or any other externally generated information which may be useful to the analytics engine 18 or analytics engine 50 External servers 16 may be hosted by third party sites and may, for example, include servers at an insurer to obtain authorizations or to facilitate reporting and billing or facilitate accident appraisals for vehicles involved in an accident.

The PSAP server 14 or other server may control or otherwise facilitate communications to and from the user device 22 or vehicle 26, a first responder ambulatory vehicle 24, PSAP personnel, and care facilities 17.

Figure 2:
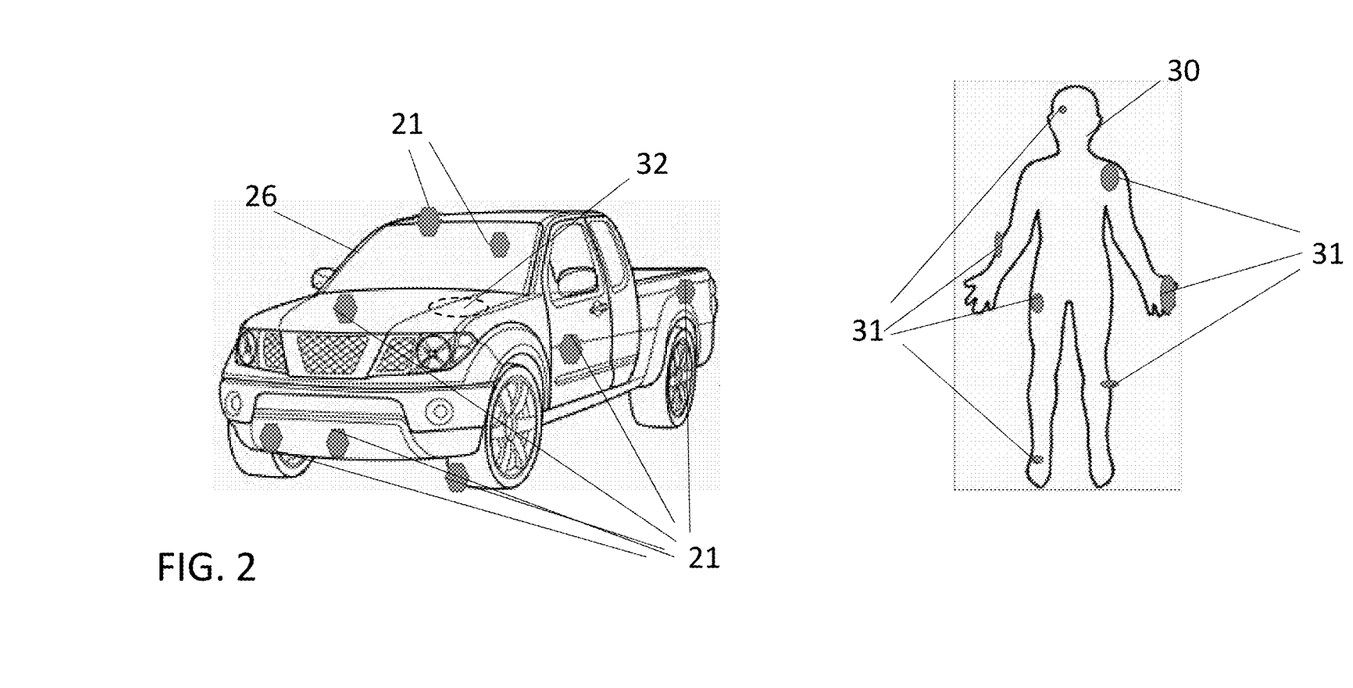
FIG. 2 is a representation of an exemplary automobile and individual having multiple sensors connected thereto.

The operating environment is further described with reference to FIG. 2 which shows multiple sensors 21 attached to vehicle 26 and multiple sensors 31 attached to the body of a person 30. The sensors 21 may, for example, include motion sensors including direction and speed, accelerometers, impact sensors, temperature sensors, vibration sensors, breakage sensors heat sensors, rollover sensors, GPS sensors, and any other sensors which may be applicable to determine the specifics of a vehicular accident. It should be noted that the location of the sensors 21 in FIG. 2 is exemplary only and the sensors 21 may be placed anywhere within the vehicle or attached to the body of the vehicle 26. The sensors 21 may also be in wireless or wired communication with a controller 22 within the vehicle 26 or an emergency application 42 further described with reference to FIG. 3 running on a smartphone 22 or tablet. The controller 22 may be placed in a convenient spot in the vehicle 26 and may, for example, be placed under the dashboard or under the hood in the engine compartment or in the trunk of the vehicle 26. The communication link between the controller 22 or emergency application 42 and sensors 21 may be a wireless communication link and may, for example, use Bluetooth®, near field communications (NFC), Wi-Fi, 4G/LTE, 5G or any other known or to be developed wireless standard. The sensors 21 may also be hardwired to controller 22.

Likewise, sensors 31 may be any type of sensors, including, but not limited to motion sensors, including direction and speed sensors, accelerometers, impact sensors, temperature sensors, vibration sensors, GPS sensors, and any other sensors which may be applicable to determine the specifics of the impact a vehicular accident may have on a person 30 traveling in the vehicle 26 or a person 30 who may have been struck by a vehicle 26. The placement of the sensors 31 shown in FIG. 2 are exemplary only and may be placed anywhere on the body of a person 30. In an aspect, the sensors 31 may also be embodied in clothing, equipment, or accessories worn by a person 30 or may be attached to the person 30 through skin adhesives or placed internally under the skin of a person 30. The particular type of sensor 31 and the placement of the sensors 31 on the body may vary and may, for example, be chosen to provide holistic data collection relating to the impact of a vehicular accident.

The above-described sensor functionality may provide a means of measuring physical forces present in a vehicular accident. Both trajectory (direction) and magnitude (speed) of forces may be measured on many points on the rider and vehicle. The more data that can be collected, the better the estimate of impact and injury prediction. As such, the functionality can be implemented with an array of small sensors placed in various locations on the vehicle and driver/rider. The sensors collect and relay data to accurately measure impact.

To be most effective, the sensors 21 and sensors 31 may collect data before, during and after a crash. Before the crash, incidents may be preventable and sensor data can be used to determine the "normal" pre-crash driving patterns and conditions. During the crash, a traumatic event that involves the exchange of energy, sensor data may measure the impacts of the exchange of energy on both the vehicle and the anatomy of the person 30. After a crash, the person 30 may enter the patient care phase and sensor data may provide vital information with respect to the patient's overall health and injuries.

Figure 3:
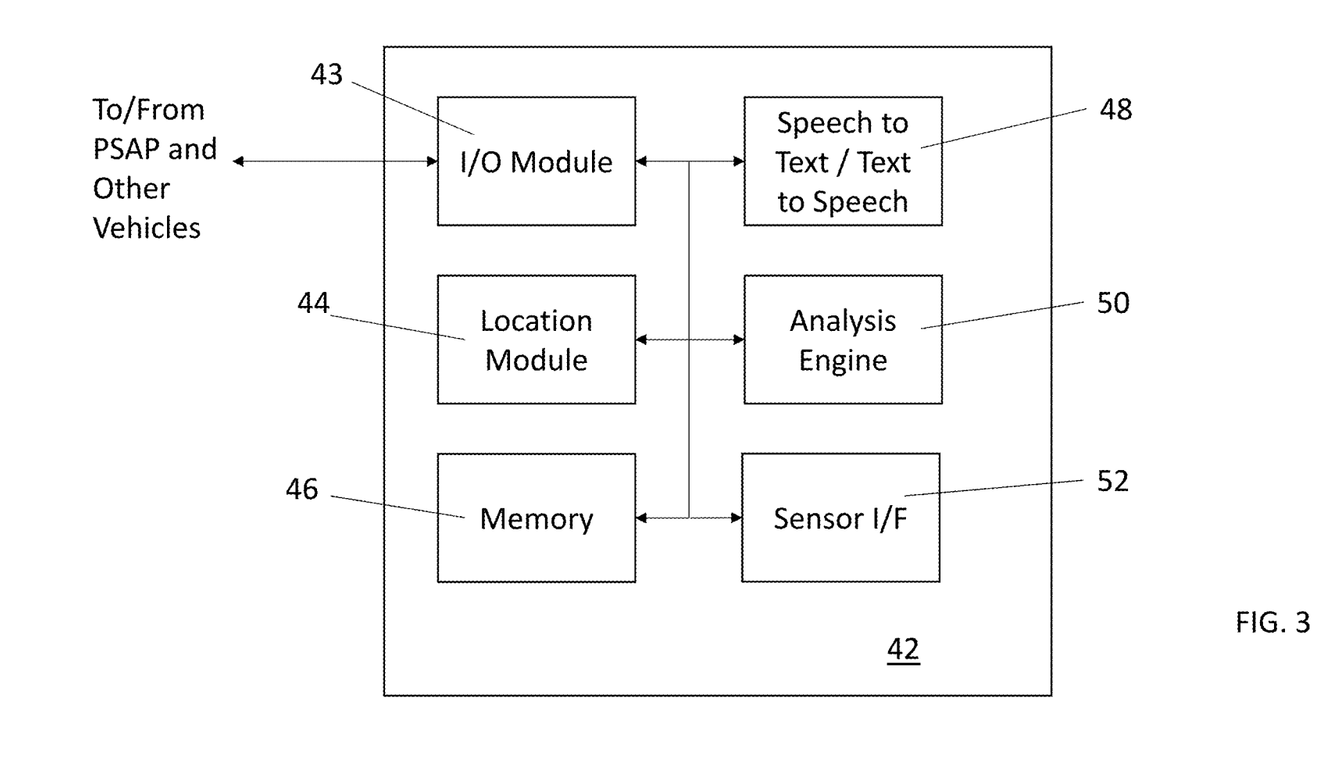
FIG. 3 is a functional block diagram of an exemplary mobile emergency application which may operate on a client such as a smartphone, tablet, portable computer or within a connected vehicle.

Emergency Application. With reference to FIG. 3, there is shown an exemplary mobile emergency application 42 (also referred to as client application herein) that may reside in a connected vehicle 26 or a user device 22. The client application 42 may include a input/output processor 43 to facilitate communications between the connected vehicle 26 or user device 22 and a PSAP server 14, occupants of the connected vehicle 26 or users of the user device 22, with other vehicles or care facilities 17. In an aspect, the input/output processor 43 may support voice and data wireless communication over 3G, UMTS, 4G/LTE, 5G, Wi-Fi, WiMax or any other wireless network. The input/output processer 43 may also interface with a keyboard, an interactive touch-screen display, a regular display, a microphone, a speaker, a mouse, touchpad, or any other input/output device. The input/output processor may also provide interfaces to sensors 21 and sensors 31, which may, for example, include communication interfaces for programming, initializing, resetting, and reading data from sensors 21 and sensors 31.

Also included in the client application 42 may include a geo-location system 44 to determine the location of the application 42, person 30, connected vehicle 26 or user device 22. The geo-location system module 44 may use GPS, a-GPS, time delay of arrival, triangulation, or any other method of determining location. The geo-location system module 44 may also receive and process GPS data from sensors 21 and sensors 31 to determine the location of a vehicle 26 or person 30 which may or may not be co-located with client application 42 or user device 22.

It may be useful for the connected vehicle 26 or the user device 22 to operate in a hands free mode, therefore a text to speech and/or a speech to text system 48 may be included in the client application 42. Using the text to speech function, a user may receive inputs from the PSAP server 14 with respect to questions relating to injuries which an operator of the client application 42 may be able to respond to. Conversely, speech to text functionality may be included in order for an operator of the client application 42, vehicle 26, or user of the user device 22 to communicate via data messaging with a PSAP server 14 or PSAP personnel or other server in a hands-free environment.

Also included in the client application 42 is a sensor interface 52. The sensor interface 52 may receive and process sensor data received from sensors 21 and/or sensors 31. Also included in the client emergency application may be an analysis module 50. The analysis module 50 may, for example, receive data inputs from sensors 21 and sensors 31 and to process those sensor data. For example, the analysis module may interpret sensor data 21 to determine the type of accident that vehicle 26 was involved in. For example, the type of accident may be a front impact, a side impact or a rollover impact, among others. The accident may include smoke or fire. The accident may have been preceded by hard breaking and deceleration, acceleration, sliding or slipping on ice or oil or other road debris. The accident may include breaking of the front windshield which for example, may indicate that a driver or passenger may have hit the windshield with their head. Interior sensors 21 to the vehicle 26 may provide additional accident information to the analysis module 50. For example, impact sensors 31 on the dashboard or door panels may indicate that a passenger has struck the dashboard or door panels. Seatbelt sensors 21 may indicate whether the seat belts were in use at the time of the accident. Air bag sensors may provide information as to whether the airbags were deployed in the accident. Lock sensors may provide information as to whether the doors are locked and whether the doors are operational. Water sensors may provide information as to whether the vehicle could be submerged.

The analysis engine 50 may, for example, also receive inputs from sensors 31 which are attached to a person 30. The sensors 31 may provide information of impacts to the person 30, for example, impacts from seat belt restraints, head impacts to the windshield, impacts on the dashboard, impacts from door panels and the like. The sensors 31 may also provide directional acceleration and deceleration data based on the type of accident. The sensors may also provide temperature data of the body and the surrounding ambient temperature which may assist on determining the presence of fire or entrapment with the windows closed on a hot summer day. It will be understood that the analysis engine 50 may receive multiple inputs from multiple sensors and sensor types for analysis and processing.

Additionally, analysis engine 50 may receive inputs from the geo-location module 44. Such location information may be useful in determining the potential injuries and perhaps the potential complications from injuries due to the remoteness of the accident, for example, or other impacts that location of an accident or the person 30 may have on the suspected injury analysis. The location module 44 may also be used by the analysis engine to request additional information from the PSAP server 14 or other external servers 16 which may, for example, include weather information, other accident or emergency information in that location, or any other relevant data.

In an aspect, the analysis engine 50 may access memory module 46. Memory module may contain historical medical data or other information on the person 30, the accident history of the vehicle 26, stored sensor data, and previous analysis.

The analysis engine 50 may also act on manual or voice inputs. For example, a non-patient at the scene of an accident may input symptoms displayed by the patient, i.e, head wounds, bleeding, broken bones, back pain, burns, or any other symptoms, and a verbal or textual description of the accident type and site, i.e., head on collision, side-swipe, car fire, explosion, or other descriptors of the accident site. The input may be via voice, text, or video. Alternatively, the analysis module 50 may collect key words input from an accident scene uttered by a user and transmit those key words to the PSAP server 14 for further analysis.

Trauma Kinematics. Trauma kinematics revolves around the impact that motion may have on injuries. The motion may, for example, be related to the motion of vehicle 26 or more subtle as in the case of the moving particles and molecules involved in injury from heat or explosions relating to an accident. By applying the laws of mechanics, the basic laws of physics, and the anatomic and material properties of the human body many of the injuries and injury patterns seen in blunt and penetrating trauma may be predicted as injury may be related to the energy of the injuring element and the interaction between that element and the victim. Although most patients suffer a unique constellation of injuries with each incident, there are quite definable and understandable energy transfer patterns that result in certain predictable and specific injuries. Knowing the details of a traumatic event may aid the treating physician to further investigative efforts to uncover occult but predictable injuries.

In an aspect, the analysis engine 50 may include an artificial intelligence (AI) element incorporating deep learning components, thereby enabling the AI engine to store a plurality of records and "learn" from interactions between the PSAP server 14, external servers 16, received sensor data and the like. The AI engine may, for example, be both predictive and prescriptive in its analytics, thereby facilitating timely forward-predictive conditions and response scenarios.

Figure 4:
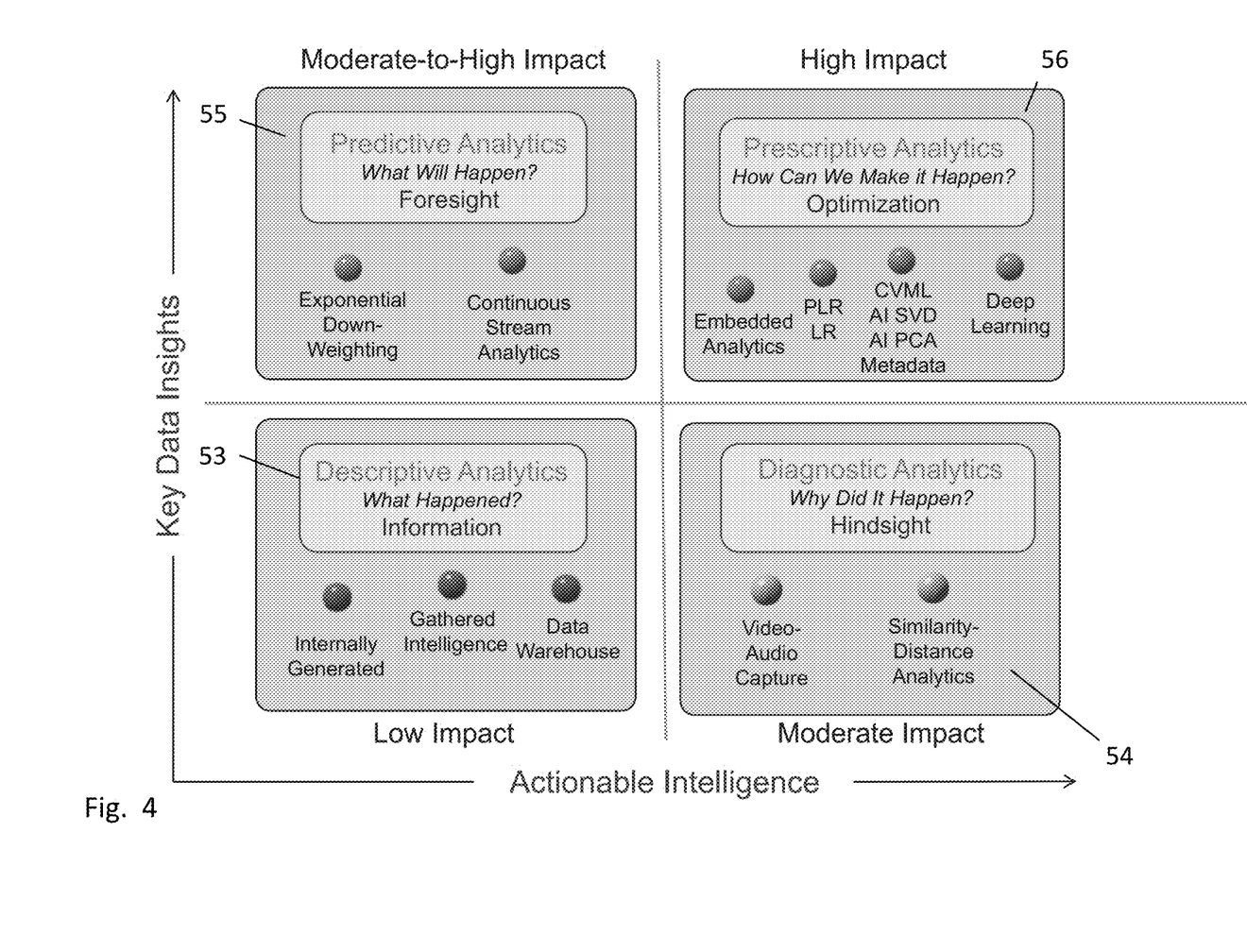
FIG. 4 is an exemplary matrix illustrating data analytics functions that may be performed in accordance with the present disclosure.

With reference to FIG. 4, there is shown an exemplary example of how big data analytics may be used on the sensor data by the analytics engine 50 to implement the concepts of trauma kinematics. There are shown four functional quadrants wherein the horizontal axis shows a continuum for actionable intelligence and the vertical axis shows a continuum for key data insights. Within the lower left quadrant, there is shown a functional box labeled descriptive analytics 53. Generally, descriptive analytics is based on past events and may, for example, be based on internally generated reports based on the collected data and other gathered intelligence. Descriptive analytics 75 may generally be directed to "what happened". In accordance with the present disclosure, the descriptive analytics performed by the analytics engine 50 may include a summary of the received data from sensors 21 and sensors 31. Such data may, for example, indicate that with respect to the vehicle 26 there was a head on collision with the vehicle traveling at 34 miles per hour resulting in deceleration to zero in 2.5 seconds with an air bag deployed. Data from sensors 31 may indicate, for example, that a person 30 involved in that accident had an impact on the left shoulder and chest and that the head of the person 30 went abruptly forward and then backward. As such, the "what happened" may include a complete description of what the sensor data showed and may, for example, include raw data or raw data formatted as a report. The report as to what happened, the data documenting the exchange of energy between the vehicle 26 and the person 30, may form the basis for the application of trauma kinematics.

To analyze "why it happened" the lower right quadrant shows an exemplary diagnostic analytics function 54. Such a diagnostic analytics function may include, for example, the analysis of inputs other than sensor inputs such as inputs from external servers 16 or inputs from the scene of an accident captured by the client application 42. For example, a slipping on ice diagnosis may inform potential injuries that differ from those potentially suffered in a head-on crash. Thus, the diagnostic function 54 may also assist in the application of trauma kinematics as the first responders and the care facility staff will understand the context of the descriptive analytics.

The diagnostic analysis 54 may, for example, include similarity-distance analytics, where similarity-distance analytics is generally defined as the "closeness" and similarity of two or more events may also include references to other similar events that happen in the past so as to correlate the previous diagnostics with the current diagnostic analysis. In the above-example, the analytics engine 50 may query memory module 46, PSAP server 14 or external servers 16 with a request for similar information that the analysis module generated by its descriptive analytics function 75. As such, the analytics engine 50 may receive data from other sliding on ice accidents or head-on collisions in the same general location and be able to compare the speed and impact points of the present situation with historical data and the analysis of that previous data. For example, the diagnostic analysis function may suggest that the head-on accident of the present example may have occurred around a steep mountain side curve or a straight stretch of highway coming out of a city. The analytics engine 50 may add this new data to the historical data to further develop the diagnostic capability for future uses in accordance with the present disclosure.

Moving to the upper left quadrant in FIG. 4, there is shown the predictive analytics function 55. The predictive analytics function 55 may fully implement the trauma kinematics analysis process. The predictive analytics function 55 may be configured to predict the diagnosis of potential injuries from the accident based on the accumulated historical data and the artificial intelligence functions which may be resident in the analytics engine 50. In the above head-on accident example, the predictive analysis function 55 may include a bruised sternum and possibly skin burns from the impact with the airbag, ligament damage to the shoulder caused by the seatbelt, and severe whiplash due to a lack of a head support in vehicle 24. The predictive analytics function 55 may, for example, include exponential down-weighting which, in an aspect, may preferentially compress a data stream into a single value that can be updated without having to save an entire dataset and in which more recently received data are weighted more than earlier-received data. This typically results in a down-weighting of older data, i.e., the data may decay over time. So as more historical diagnostic data are accumulated and the diagnosis becomes more accurate, it is those more recent diagnosis that will be weighted more heavily by the analytics engine 50 and thereby improve the predicted injuries from an accident. Additionally, continuous stream analytics provide the foundation for fast adaptive actions based on complex event processing and event stream processing, permitting data to be processed before it lands in memory 40 or uploaded to database 20. This predictive analytics function 55 may support much faster decision making than possible with traditional data analytics technologies such as descriptive analytics 53 and diagnostic analytics 54. In other words, the predictive analytics function 55 may constantly be calculating the potential injuries sustained by a person 30 while managing and monitoring live streaming data from sensors 30 and sensors 31. The data being operated on may also include other information described above which is accessible to the analytics engine 50.

Finally, with respect to the upper right quadrant of FIG. 4, there is shown a prescriptive analytics function 56 which may, for example, optimize future outcomes in emergency scenarios. This function may be applied during the emergency event or after the emergency event has been handled. The analytics engine's 50 prescriptive analytics elements function 78 may include, for example, embedded analytics in which analytic functions are integrated within various operational processes to improve the efficiency of those operational processes. For example, in the event that the injury to person 30 includes broken ribs and severe whiplash from the accident, the analytics engine may interact with the PSAP server 14, first responder vehicles 24 and care facility 17 to not only communicate the potential injury to person 30, but to also proactively develop a treatment protocol and a transportation route to optimize the patient outcome. The results of this treatment may result not only in improved predictive injuries, but also improve the standard of care involved in treating kinematic trauma.

The prescriptive analytics elements function 56 may also include predictive linear regression (PLR) in which an outcome is predicted based on a change of one of the input variables in terms of numeric and categorical inputs (dependent, or response variable), and logistic regression (LR), in which a binary outcome may be predicted based on an analysis of the input variables, where a probability is predicted that an instance belongs to a specific category, for example, the probability that a particular type of vehicle accident would cause a specific type and level of injury. For example, regression analysis may permit testing of a particular treatment to achieve a likely outcome and the effect a different treatment may have on the likely outcome. The PLR and LR elements may incorporate nearest-neighbor predictive algorithms (where 'nearness' may be basic Euclidean distance with resultant utility in selecting non-duplicate variables, rescale variables, and orthogonalizable variables). By way of further example, prescriptive analytics elements function 78 may also include continuous variable machine logic (CVML) which may include, for example, other statistical based functions including AI-based singular value decomposition (SVD), AI-based principal component analysis (PCA), and metadata. CVML may also include predictive linear regression. Deep learning functionality in which a cascade of processing layers may be analyzed layer by layer may also be used in the prescriptive analytics elements function 56.

It will be understood that these functions are exemplary only and other statistical methods and functionality may be used to implement any of the trauma kinematics diagnostic functions of the analysis engine 50. It will also be understood that some or all of the analytical processing may be off-loaded to a remote server from the client application which remote server may, for example, include the PSAP server 14 or other external servers 16, which will collectively be referred to as analysis servers unless the context indicates otherwise.

PSAP server 14 and/or other analysis servers and the client application 42 may each be implemented as a general purpose computer programmed to provide the functions set forth above, and as such, each may have a CPU function and a memory for storing executable instructions thereon. It will be understood by those skilled in the art that some or all of the analysis functions described above with respect to the client application 42 may be performed by an application running on the PSAP server 14 or analysis servers or any other server or processor in communication with PSAP server 14. In either case, as much information as is reasonably practical under the circumstances that is conveyed from the sensors 21 and sensors 31 from an accident or incident site to the PSAP server 14 will assist in optimizing the predicted injuries of a person 30 involved in the accident.

Figure 5:
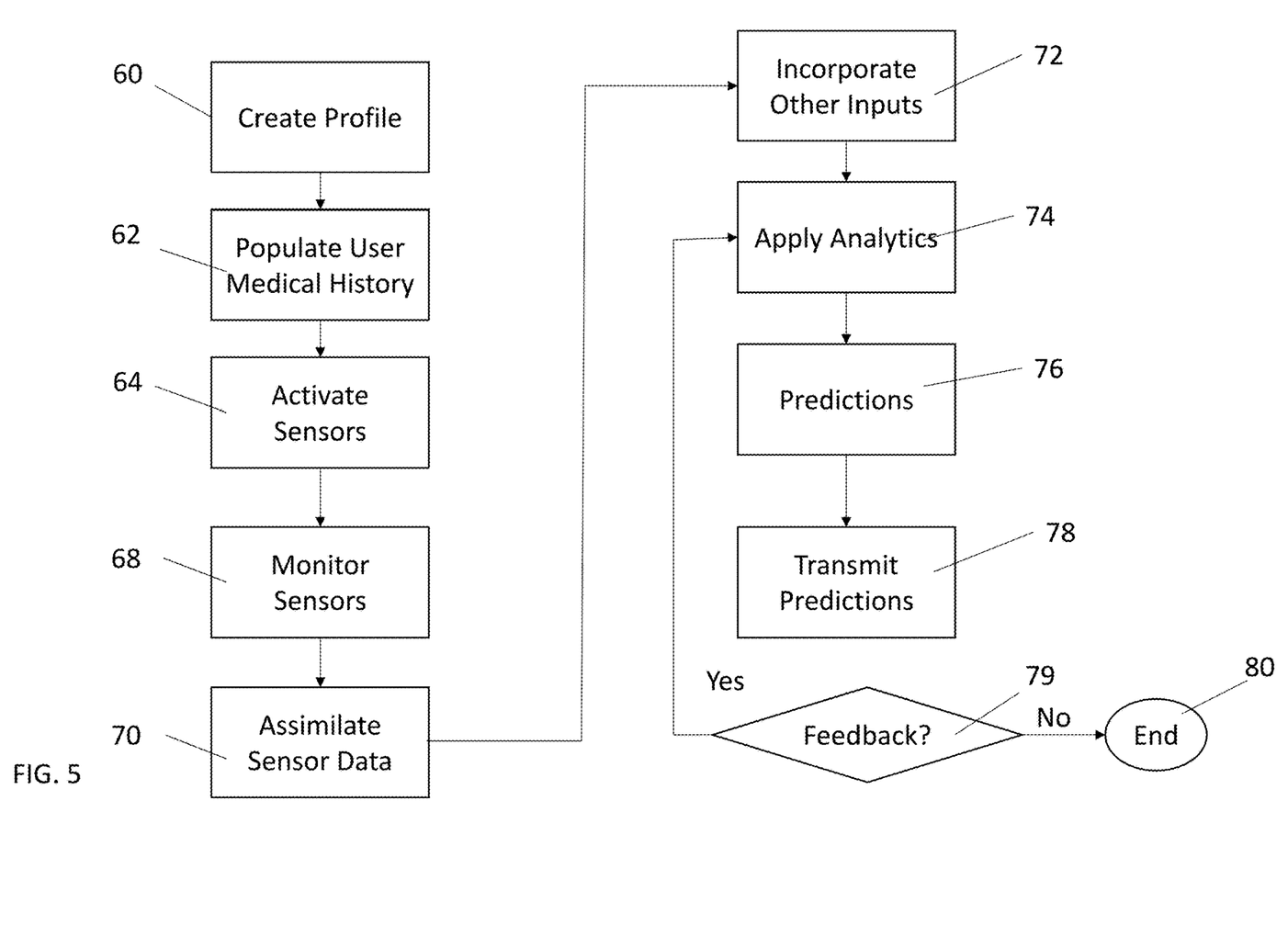
FIG. 5 is an exemplary flow diagram of a process which may be performed by an application in accordance with the present disclosure.

Methods of Use. With reference to FIG. 5, there is shown a flow chart of the system and method of the present disclosure in operation. At 60, a user profile is created. Such a profile may be created through an on-line portal or other input mechanism. The patient profile may reside in a client application 42, database 20, storage associated with a different analysis server, or any other storage means. Such user information may, for example, include the patient's age, gender, height, weight, (or approximations of the foregoing)

or any other general information about the patient. At 62, the user's medical history may be populated, either received from an external server or populated directly by the user. At 64, sensors, as described in detail above, are activated. At 68, the sensors are monitored during an event and sensor data received by a client application. At 70, sensor data are assimilated. At 72, additional information about the patient from other inputs may be incorporated. For example, additional information may include the key words describing the suspected injuries or the preliminary analysis of the patient injuries by a either the person or a witness or other bystander. At 74, analytics as described by the example above are applied. At 76 predictions as to the potential injuries and severity of those injuries are performed. At 78, the predictions are conveyed to a PSAP server 14, a first responder vehicle 24 or any other site, provider or institution, including auto or health insurers, auto body shops or the like, collectively a destination. The predictions may may be communicated via voice, video, data or text or some other messaging application to the destination or destinations. In the event of a multiple injury situation, the process may be repeated serially or in parallel for each patient and the analysis may include any common facts associated with the multiple injuries or multiple plaintiffs. The analysis that is conveyed may also include a severity index which may, for example, designate injuries as being on the continuum from minor to severe to life threatening, depending on the symptoms and predicted injuries.

In an aspect, the system and methods of the present disclosure may transmit a predictive injury report to a medical team or analysis server which analyzes the injury report and then provides feedback at 79 to the client application 42. For example, an analysis server receiving the predictive injury report may detect an ambiguity that requires clarification or may request additional analysis or reports from one more particular sensors 21 or sensors 31. As such, the method may revert back to 74 for the application of additional analytics whereby some or all of the methods of the present disclosure may be used iteratively with the feedback provided from an external source. If there is no feedback at 79, the process ends at 80.

While examples of a system and method in which potential injuries may be automatically diagnosed in real-time or near real time have been described in connection with various computing devices/processors, the underlying concepts may be applied to any computing device, processor, or system capable of facilitating a telecommunications system. The various techniques described herein may be implemented in connection with hardware or software or, where appropriate, with a combination of both. Thus, the methods and devices may take the form of program code (i.e., instructions) embodied in concrete, tangible, storage media having a concrete, tangible, physical structure. Examples of tangible storage media include floppy diskettes, Compact Disc-Read-Only Memory devices (CD-ROMs), Digital Versatile Discs, or, Digital Video Discs (DVDs), hard drives, or any other tangible machine-readable storage medium (computer-readable storage medium). Thus, a computer-readable storage medium is not a signal. A computer-readable storage medium is not a transient signal. Further, a computer-readable storage medium is not a propagating signal. A computer-readable storage medium as described herein is an article of manufacture. When the program code is loaded into and executed by a machine, such as a computer, the machine becomes a device for telecommunications. In the case of program code execution on programmable computers, the computing device will generally include a processor, a storage medium readable by the processor (including volatile or nonvolatile memory or storage elements), at least one input device, and at least one output device. The program(s) can be implemented in assembly or machine language, if desired. The language can be a compiled or interpreted language, and may be combined with hardware implementations.

The methods and devices associated with the disclosure described herein also may be practiced via communications embodied in the form of program code that is transmitted over some transmission medium, such as over electrical wiring or cabling, through fiber optics, or via any other form of transmission, over the air (OTA), or firmware over the air (FOTA), wherein, when the program code is received and loaded into and executed by a machine, such as an Erasable Programmable Read-Only Memory (EPROM), a gate array, a programmable logic device (PLD), a client computer, or the like, the machine becomes an device for implementing telecommunications as described herein. When implemented on a general-purpose processor, the program code combines with the processor to provide a unique device that operates to invoke the functionality of the system described herein. Functions described as operating on a client device may be operating on a server and vice versa.

It will be apparent to those skilled in the art that various modifications and variations may be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for predicting injuries comprising:
   a plurality of sensors configured to generate sensor data, wherein the sensor data include data from a vehicle obtained from a vehicle-mounted sensor;
   an input-output interface; and
   a processor coupled to the input-output interface and wherein the processor is coupled to a memory, the memory having stored thereon executable instructions that when executed by the processor cause the processor to effectuate operations comprising:
   receiving stored information from a database, wherein the database includes medical history of an occupant of a vehicle and historical sensor data;
   receiving the sensor data;
   identifying changes in the sensor data based on a comparison to expected sensor data and to historical sensor data;
   applying predictive linear regression analytics to the sensor data based on the identifying step to create analyzed sensor data;
   based on the applying step, predicting a likely injury to the occupant of the vehicle involved with an event associated with the vehicle;

transmitting a report comprising the medical history and the likely injury to the occupant of the vehicle based on the predicting step.

2. The system of claim 1 wherein the predicting step comprises applying trauma kinematics analysis to the analyzed sensor data.

3. The system of claim 1 wherein the plurality of sensors further comprise person-mounted sensors mounted on clothing of the occupant of the vehicle and wherein the sensor data also includes second sensor data from the person-mounted sensors.

4. The system of claim 1 wherein the operations further comprise receiving additional data inputs from an external server and the applying step comprises applying predictive linear regression analytics to a combination of the analyzed sensor data and the additional data inputs.

5. The system of claim 4 wherein the additional data inputs comprise one of text inputs, voice inputs and screen inputs.

6. The system of claim 1 wherein the operations further comprise recording the likely injury in the memory.

7. The system of claim 1 wherein the transmitting step comprises transmitting the report to one of a care facility and a first responder.

8. The system of claim 7 wherein the stored information from the database also includes capabilities of the care facility.

9. A method comprising:
receiving historical medical data of an occupant of a vehicle;
receiving sensor data from a plurality of sensors, wherein at least one of the plurality of sensors is a vehicle-mounted sensor associated with the vehicle and at least another one of the plurality of sensors is an occupant-mounted sensor associated with the occupant of the vehicle wherein the occupant-mounted sensors are configured to monitor movements of the occupant of the vehicle;
identifying changes in the sensor data based on a comparison to expected sensor data;
analyzing the changed sensor data using predictive linear regression analytics;
applying trauma kinematics to the analyzed sensor data;
predicting an injury to the occupant of the vehicle based on the applying step; and
transmitting a report comprising the predicted injury and the medical history.

10. The method of claim 9 wherein the transmitting step comprises transmitting the report to one of a care facility and a first responder.

11. The system method of claim 10 further comprising storing in a database capabilities of the care facility.

12. The method of claim 9 further wherein the sensor data is received wirelessly by an application operating in a controller.

13. The method of claim 12 wherein the controller is a user device.

14. The method of claim 12 wherein the controller is located within a connected vehicle.

15. The method of claim 9 wherein the sensor data are compared to historical sensor data.

16. The method of claim 15 further comprising comparing the predicted injury to an historical record of injuries.

* * * * *